United States Patent [19]

Woodward

[11] Patent Number: 5,074,786

[45] Date of Patent: Dec. 24, 1991

[54] INTRAORAL MEDICATION RELEASING SYSTEM

[75] Inventor: Kathleen A. Woodward, San Diego, Calif.

[73] Assignee: Johnson & Johnson Consumer Products, Inc., Skillman, N.J.

[21] Appl. No.: 502,349

[22] Filed: Mar. 30, 1990

[51] Int. Cl.$^5$ .......................................... A61C 19/06
[52] U.S. Cl. ...................................... 433/80; 433/229
[58] Field of Search ................. 433/80, 229, 11, 10; 604/285, 891.1; 40/649, 650; 24/545

[56] References Cited

U.S. PATENT DOCUMENTS

| | | | |
|---|---|---|---|
| 589,712 | 9/1897 | Fouquier | 604/77 |
| 1,622,616 | 3/1927 | Temple | |
| 1,642,653 | 9/1927 | Goldstein | |
| 1,934,688 | 11/1933 | Ackerman | 32/5 |
| 3,043,006 | 7/1962 | Wallshein | 433/11 |
| 3,327,393 | 6/1967 | Brader | 433/11 |
| 3,421,221 | 1/1969 | Silverman et al. | 32/14 |
| 3,527,218 | 9/1970 | Westline | 128/229 |
| 3,600,807 | 8/1971 | Sipos | 32/2 |
| 3,624,909 | 12/1971 | Greenberg | 32/40 |
| 3,688,406 | 9/1972 | Porter et al. | 32/40 |
| 4,020,558 | 5/1977 | Cournut et al. | 32/40 |
| 4,021,921 | 5/1977 | Detaille | 32/40 |
| 4,023,274 | 5/1977 | Wallshein | 433/11 |
| 4,077,126 | 3/1978 | Pletchar | 433/10 |
| 4,103,423 | 8/1978 | Kessol | 433/10 |
| 4,106,501 | 8/1978 | Ozbey et al. | 128/62 |
| 4,175,326 | 11/1979 | Goodson | 433/80 |
| 4,412,825 | 11/1983 | Tokarz | 433/229 |
| 4,465,462 | 8/1984 | Ticknor | 433/136 |
| 4,492,573 | 1/1985 | Hanson | 433/11 |
| 4,523,910 | 6/1985 | Makovich | 433/80 |
| 4,560,351 | 12/1985 | Osborne | 433/80 |
| 4,614,497 | 9/1986 | Kurz | 433/10 |
| 4,671,768 | 6/1987 | Ton | 433/174 |
| 4,681,544 | 7/1987 | Anthony | 433/215 |
| 4,685,883 | 8/1987 | Jernberg | 433/215 |
| 4,741,700 | 5/1988 | Barabe | 433/229 |
| 4,861,268 | 12/1989 | Garay et al. | 433/229 |
| 4,892,483 | 1/1990 | Douglas | 433/229 |
| 4,959,052 | 9/1990 | Cox | 430/80 |

FOREIGN PATENT DOCUMENTS 2357573  5/1975  Fed. Rep. of Germany ........ 433/11

OTHER PUBLICATIONS

Hanes et al., "Effective Delivery Systeems for Prolonged Fluoride Release: Review of Literature", JADA, vol. 113, pp. 431–436, Sep. 1986.

Mirth, "Controlled-Release Therapeutic Systems: Technology Applicable to the Treatment of Oral Disease", Adv. Dent. Res. 1, pp. 109–118, Oct., 1987.

Cowsar, "Introduction to Controlled Release", Research Paper, pp. 1–13.

*Primary Examiner*—Paul J. Hirsch
*Attorney, Agent, or Firm*—Paul A. Coletti

[57] ABSTRACT

Aa system for long term releasing of medication in the mouth, and especially an intra-oral fluoride releasing system (IFRS) for releasing fluoride over a long term for inhibiting the formation of caries in the teeth. The system uses a holder for retaining and protecting intra-oral fluoride tablets or other intra-oral medicament in the form of fluoride releasing devices (IFRD). The holder has a plate with retaining sides and retaining posts or a carrier. The tablet will fit within the holder. The tablet may be located in the carrier, or ligature bands can be tied around the tablet in order to releasably hold the IFRD within the holder. The system causes a level of fluoride to be maintained over a long term within the mouth which has been found chemically effective for caries control and without causing severe irritation to oral tissues. In another embodiment, the user of an orthodontic bracket is provided with a system where a post is attached to the orthodontic appliance, perhaps at the archwire slot, and the IFRD is placed within the mouth at a site removed from the orthodontic brackets themselves. This unique combination provides for better oral hygiene and yet delivery of a fluoride to the mouth through the IFRD.

4 Claims, 4 Drawing Sheets

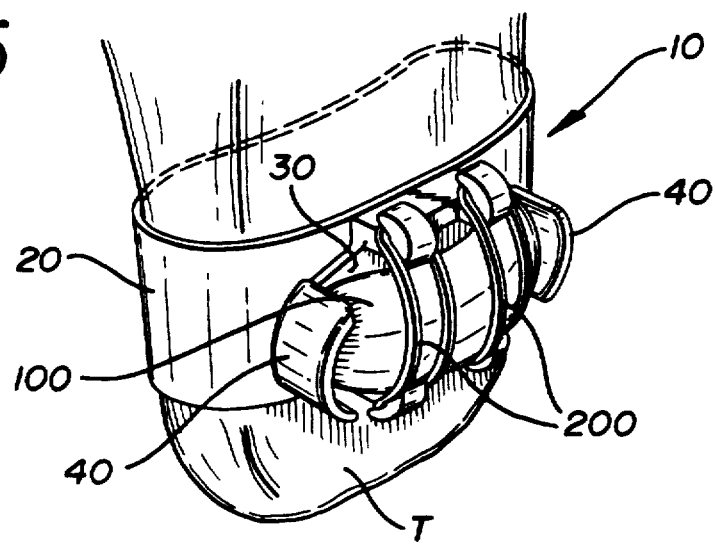
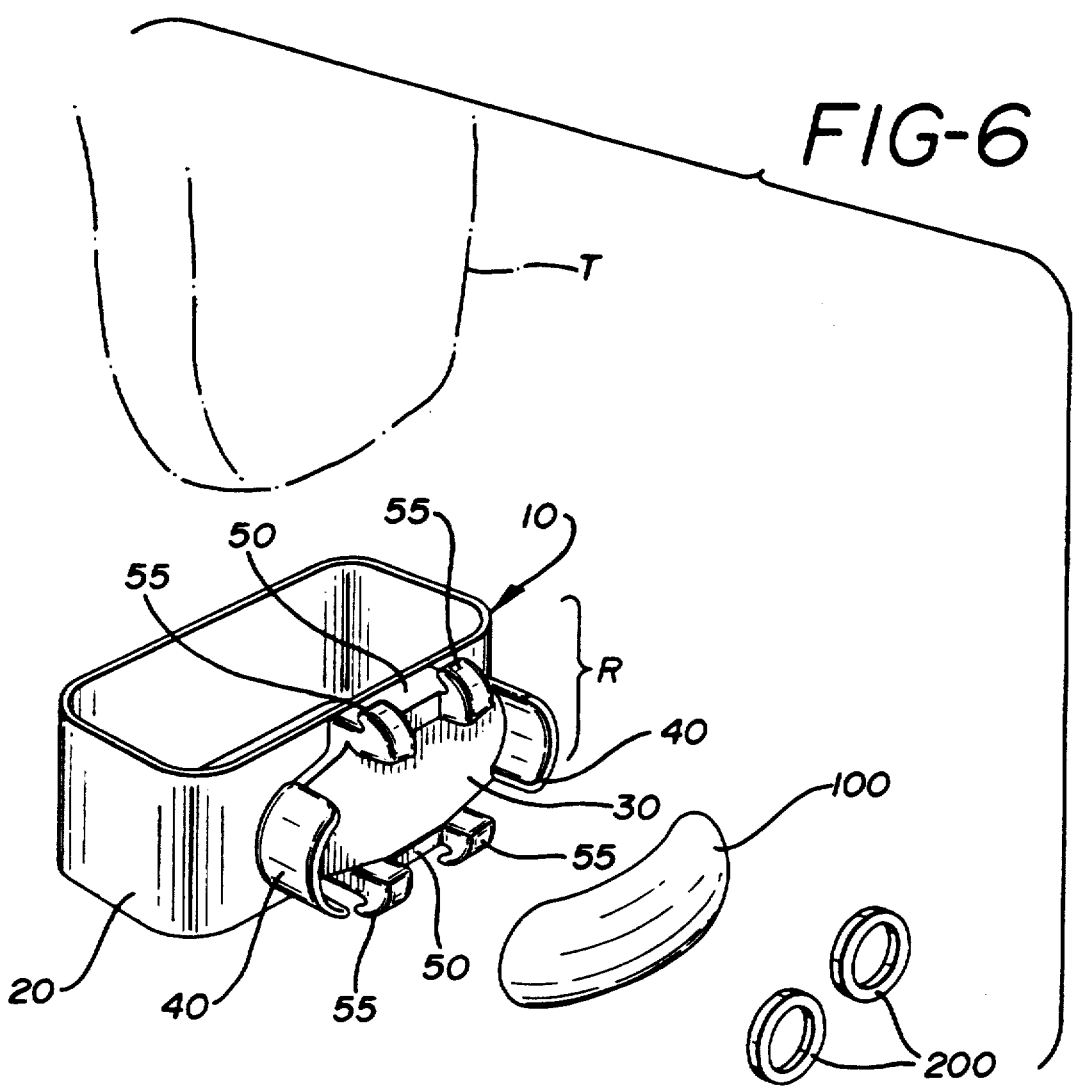

INTRAORAL MEDICATION RELEASING SYSTEM

FIELD OF THE INVENTION

This invention relates generally to systems for retaining and dispensing caries preventative media (fluoride) intraorally for sustained-controlled release to the teeth by the saliva over a long period of time (weeks or months) and to holders for use within the mouth which retain and protect an intra-oral fluoride-releasing device (IFRD). The combination of an IFRD and its holder comprises an intra-oral flouride-releasing system (IFRS). This invention is generally useful in intra-oral medication holders for long term timed release tablets of medication in the mouth without significant irritation of oral tissue.

BACKGROUND OF THE INVENTION

Dental research has had remarkable success in dental caries prevention. Specifically, it has been found that roughly fifty percent of children ages six through seventeen living in the United States are caries free. This remarkable progress during the last twenty years is due, in part, to better oral hygiene, use of fluoridated water, and fluoridated products, i.e., dentifrices. Nevertheless, there are patients who remain susceptible to dental caries. For instance, twenty percent of all children account for roughly sixty percent of all carious lesions. Also, certain subjects with diminished salivary functions are especially prone to caries, because they produce limited amounts of saliva. Other risk factors, such as poor oral hygiene, physical or mental handicaps, and certain systemic diseases or disorders may also predispose individuals to dental caries.

Recent studies have demonstrated that elevated concentrations of fluoride in the mouth for extended periods will help reduce caries. A source of such fluoride is contained in controlled-release fluoride tablets which have been called intra-oral fluoride releasing devices (IFRD's). These IFRD's release fluoride into the oral cavity for extended periods up to six months to enhance prevention of dental caries.

Previous attempts to retain IFRD's in the mouth have failed for a variety of reasons. For instance, IFRD's produced by Southern Research Institute were designed to be bonded directly to the teeth. These IFRD's were found susceptible to debonding from masticatory forces or were subject to excessive wear caused by abrasives contained in toothpastes. What is desirable, therefore, is a system whereby IFRD tablets can be safely secured and retained in the mouth until their fluoride supply is exhausted.

Additionally, in patients with orthodontic brackets, it is more difficult to practice oral hygiene while supplying regular fluoride treatment to the patient. This is especially true because when the patients are using orthodontic brackets, any attachments to the teeth other than the orthodontic brackets are difficult, or even impossible.

In addition, it is desirable to have a system (an intra-oral fluoride release system or IFRS) whereby the tablets can be replaced periodically following depletion of their fluoride content. It is further desirable for these systems to be broadly useful for children undergoing active orthodontic treatment. In general these children have an increased risk to caries development because they are not able to adequately brush their teeth. It is also desirable to provide an IFRS which does not cause severe irritation to mouth tissues. What is meant by severe irritation is ulceration or acute inflammation which interferes with oral function and nutrition, such as pain, induration or necrosis or purulent exudate from tissue in the vicinity of the IFRS.

SUMMARY OF THE INVENTION

Accordingly, it is the principal object of this invention to provide an IFRS whereby the foregoing problems and needs are resolved and more particularly to provide intra-oral IFRD holders which can be safely placed and securely retained in the mouth for an indefinite period.

It is another object of the invention to provide an intra-oral fluoride releasing system to patients who wear orthodontic brackets.

Briefly described, a system according to the invention comprises a holder which has a retaining member, such as a plate or band with a back surface adapted to be disposed on a surface of a tooth. This back surface is connected to a pair of opposed retaining sides within which the tablet can be placed, either directly on the plate, or in a carrier releaseably connected to the plate. At the ends of the opposed retaining sides are a pair of retaining posts. These posts can be wrapped with ligatures, which extend over the tablet so that the tablet is exposed in the mouth but remains in place within the holder. An openable cover may be mounted on and extend across the retaining side. Fluoride is delivered to the oral cavity by the IFRD tablets at therapeutic levels continuing for up to six months. The IFRD can be replaced by removing and replacing the ligatures or opening the cover, removing and reinserting the holder with a fresh fluoride carrier, or replacing the system (the IFRD and the holder) in its entirety.

Furthermore, in an effort to treat patients with orthodontic brackets, IFRD's are provided where the fluoride device is attached to a fluoride carrier holding mechanism which in turn, is attached to the orthodontic device. Alternately, the fluoride releasing system is configured so that the fluoride tablet is attached remotely to the bracket itself.

These and other objects and embodiments of the invention will be better understood with the attached figures and detailed description of the drawings, in which:

DETAILED DESCRIPTION OF THE DRAWINGS

FIG. 5 is a perspective view of an embodiment in accordance with the invention shown attached to a tooth;

FIG. 6 is an exploded perspective view of the embodiment of the invention shown in FIG. 5 fluoride tablet;

DETAILED DESCRIPTION OF THE INVENTION

Figure 7:
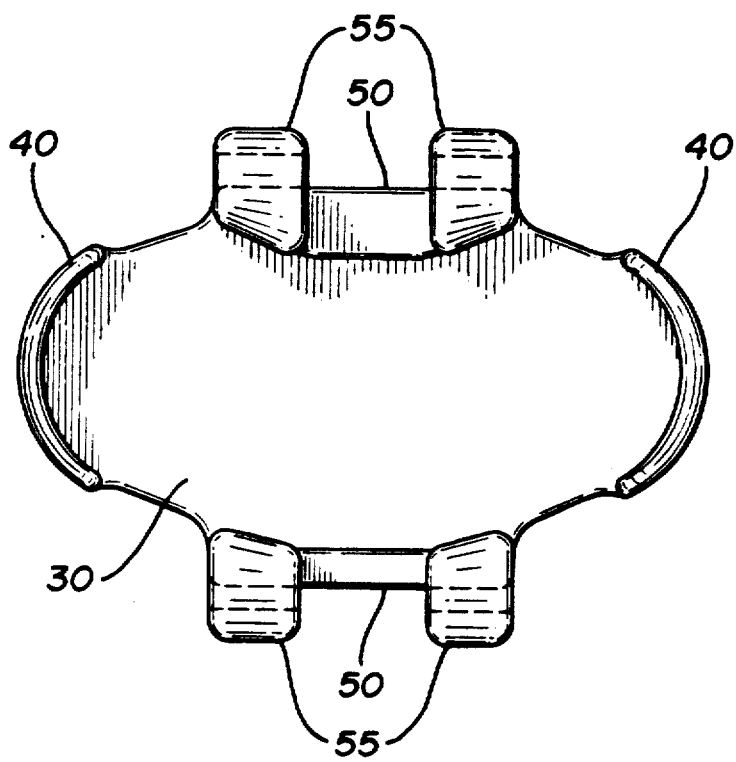
FIG. 7 is a top view of the retaining member of the holder of the embodiment of the invention shown in FIG. 5.
Figure 8:
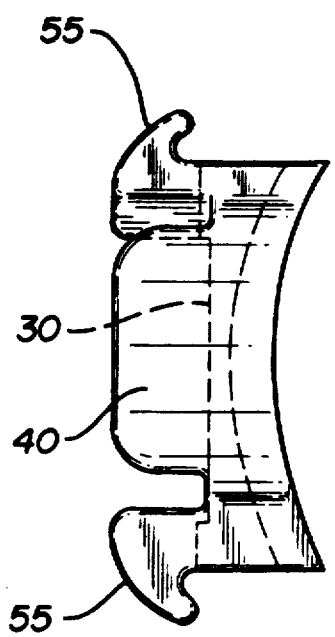
FIG. 8 is a side view of the retaining member shown in FIG. 7.
Figure 9:
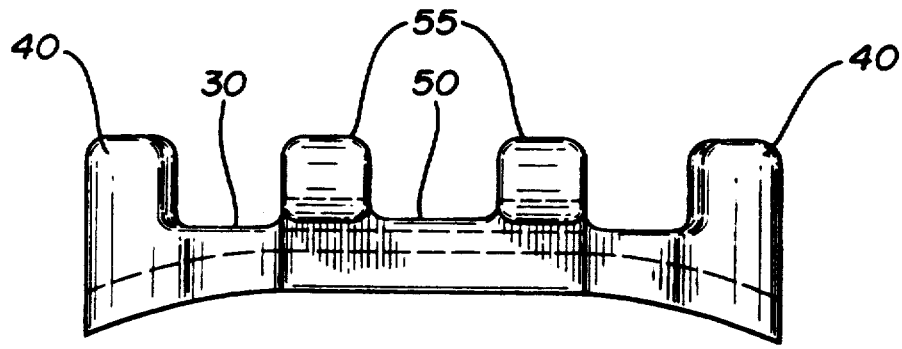
FIG. 9 is a front view of the retaining member shown in FIG. 7.

As seen from FIGS. 5, 6, 7, 8 and 9, there is provided in accordance with a first embodiment of the present invention, an IFRS having a holder 10 for fluoride impregnated carriers or tablets which will be emplaced in the mouth. These tablets are generally controlled release fluoride tablets and are oval or kidney bean shaped such as tablet 100 as seen in FIG. 6. The holder 10 is generally comprised of a band 20 which wraps around the tooth and a retaining member R. This retaining member R will generally be formed of a plate 30 having back surface which is attached, as by spot welding, to the band 20. The member R has retaining sides 40, as best seen in FIGS. 6 and 7. The tablet 100 generally fits snugly within the retaining sides 40 and against the anterior surface of the holder 10. The posterior surface of the plate may be cusp shaped to conform to the outer surface of the tooth, or affix directly to the tooth surface.

In order to secure the attachment of the tablet 100 to the holder 10, the plate 30 has a pair of retaining posts 50. These posts 50 have knob-like projections 55, usually with indentations around which miniature elastic bands, known as ligature bands 200, can be attached. When the tablet 100 is inserted into the holder 10, the ligature bands 200 are placed around the knobs 55 so that they snugly hold the tablet 100 within the holder 10, as seen best in FIG. 1. The band 20 then is generally applied around the tooth. Instead of ligature bands, stainless steel ligature wires may be used, and the term ligatures or ligature bands should be taken as encompassing both endless bands and wires.

The method of application will proceed as follows: The tooth generally will have separators placed into the interdental spaces to gain dental ligament space so as to insert the band 20. The band 20 is then inserted around the tooth and made to fit snugly. The tablet 100 is placed onto the plate 30 of the holder 10. The ligature bands or wires 200 are placed around the retaining post knobs 55 and allow the tablet to be releaseably retained and protected in the mouth. As can be appreciated, if the intra-oral fluoride tablet 100 is broken in the mouth or releases its fluoride content, the ligature bands 200 can be removed, and a new tablet 100 can be inserted into the holder 10. In this way, the holder 10 can achieve any necessary permanence in the mouth dependent upon the desired dental procedure.

Figure 1:
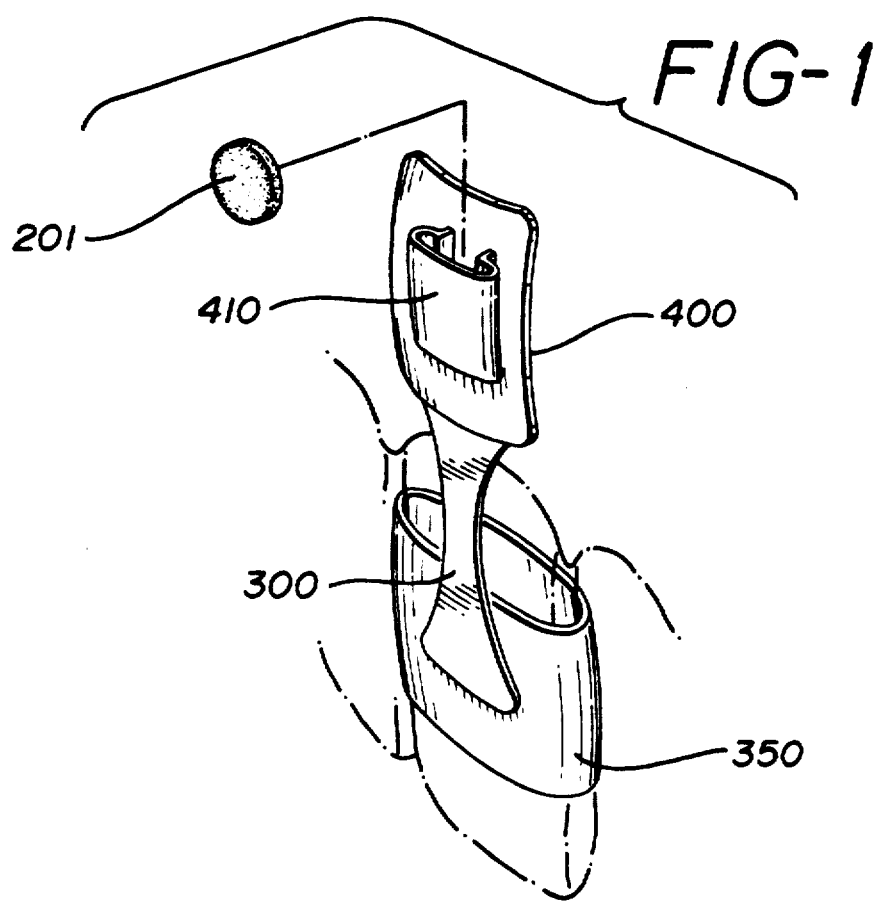
FIG. 1 is a perspective view of an IFRS.
Figure 3:
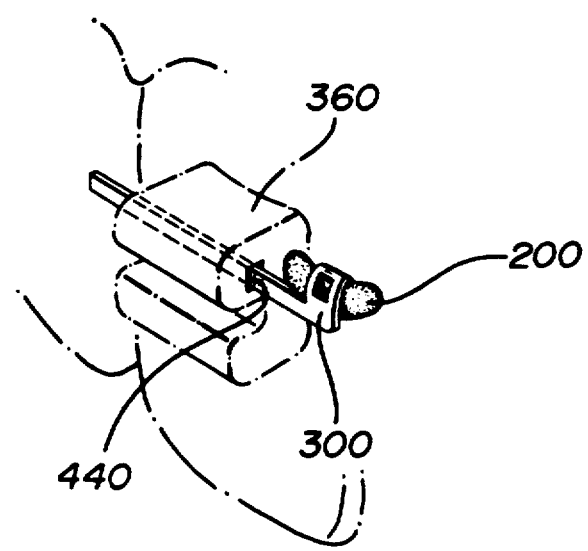
FIG. 3 is a perspective view of a means for attaching part of the system for use with orthodontic brackets.

As seen in FIG. 1, another IFRD system may contain a post or stem 300, which may be directly bonded to the tooth surface. This post or stem 300 may be welded onto a band 350 or pad 400, or attached to an orthodontic device or dental appliance 360, as seen in FIG. 3. The post or stem 300 may be one or two-piece system and used for all holders. It allows the holder as later described to be placed away from the tooth surface and up under the lips and away from the gingiva. In this way, the IFRD is able to release fluoride which will remain in the mouth for a longer period of time, as it will not be washed away more quickly by saliva.

Extending from the post or stem 300, is a holder useful for placement of a IFRD. This holder is generally a flat, curved plate 400 which contains a pocket 410 into which an IFRD 201 is inserted.

Figure 2:
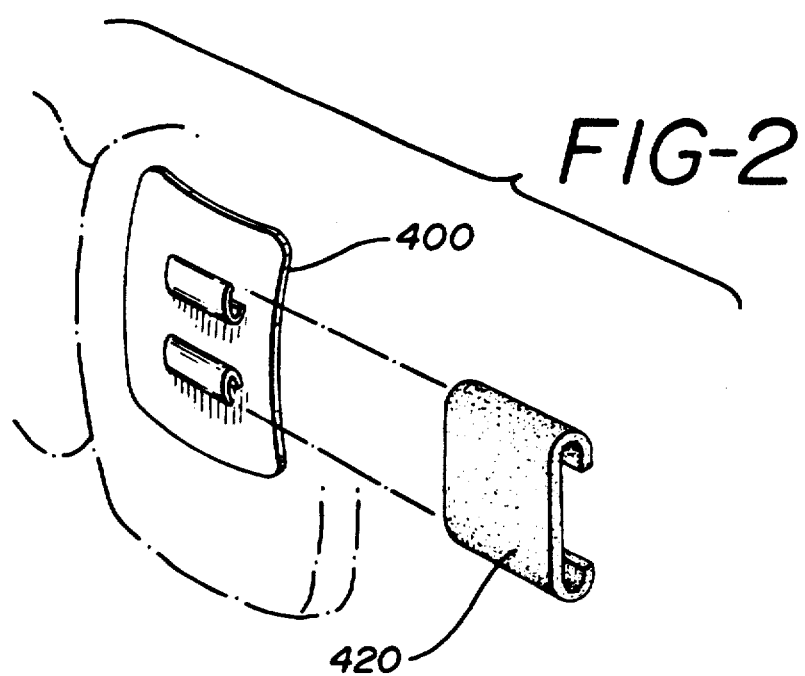
FIG. 2 is a perspective view of an alternate embodiment for an IFRS.
Figure 4:
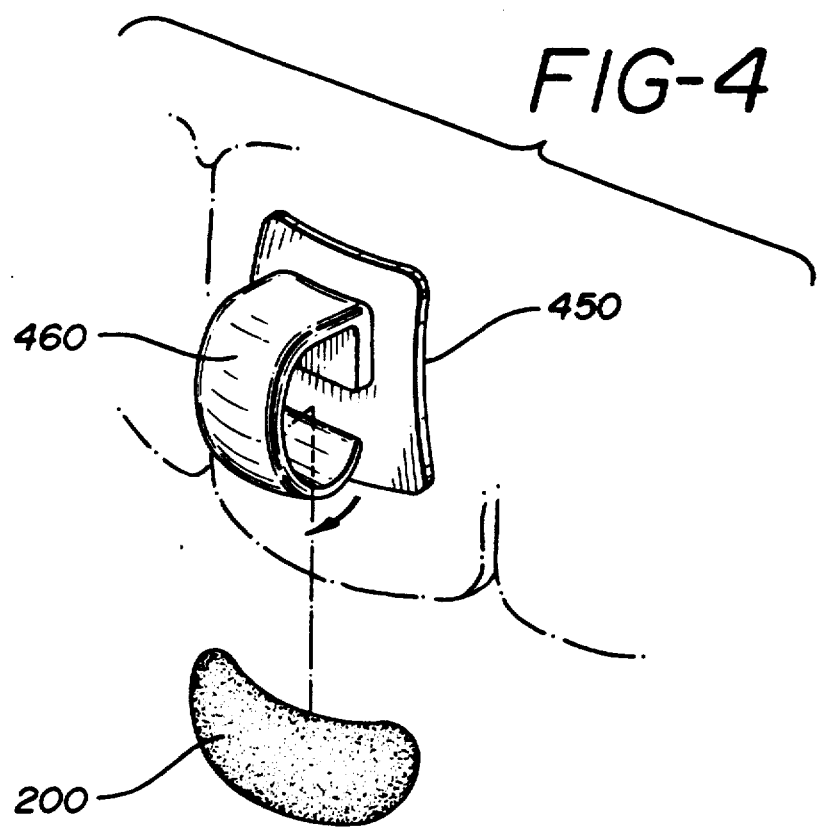
FIG. 4 is a perspective view of a IFRD holding mechanism useful singularly or in combination with the IFRS of FIG. 1.

Other pockets which embody clips or other holding devices like sliding mechanisms are better seen in the drawings in FIGS. 2 and 4. In FIG. 2, for instance, if the patient is not wearing orthodontic brackets, there may be directly bonded onto the tooth a pad (as in FIG. 1) 400 which allows insertion of a formed fluoride composite 420 impregnated with fluoride. This composite may be mounted within the pad, either horizontally or vertically and is able to release fluoride directly from the tooth.

Alternately, as in FIG. 4, an IFRD patch 200 may be snapped into a holding mechanism 450 from any direction, usually the bottom. This holding mechanism 450 has a hook-shaped clasp 460 which embraces in a spring-like relationship, the sides of the IFRD 200, but allows the edges of the IFRD 200 to release fluoride into the system.

The mechanism forming clasp 460 of FIG. 4 may be placed directly on the tooth, or used in connection with a post or stem 300 as in FIG. 1. Clasp 460 may also contain hydration vents not shown.

On the other hand, as seen in FIG. 3, the attaching mechanism post 300 may be inserted into a snap-type tube 440 attached to the orthodontic bracket 360. This allows the kidney bean-shaped IFRD 200 to be attached to the tube 360 and disperse fluoride into the mouth. Alternately, the formed fluoride composite as in FIG. 2, may be inserted into the pocket-type holder 410 away from the orthodontic bracket and into the gingiva, in connection with the post 300 of FIG. 3.

In all these ways, the user of orthodontic brackets is able to receive fluoride in equivalent dosages as the non-orthodontic bracket patient.

It should be noted that all the holder embodiments are preferably made of a high strength aluminum or other metal (e.g., stainless steel) or, in the alternative, a non-degradeable bio-compatible hardened plastic. The material withstands masticatory forces in the mouth, yet still allows large open areas of contact with the saliva to allow release of fluoride to the oral cavity.

What is claimed:

1. A system for replaceably receiving intra-oral tablets comprising:
   a holder having a plate with an anterior surface and defining a space within which said tablets are individually emplaced;
   means attached to said plate for removably retaining said tablet and generally preventing movement of said tablet from said holder; and
   post means, wherein said holder is attachable at said post means to an orthodontic bracket.

2. A system for replaceably retaining an intra-oral controlled release medication impregnated patch in the mouth, comprising:
   a medicated patch with a continuous planar surface having engaging means;
   a holder having a plate for attachment to a tooth;
   said patch attachable to said plate; and
   said holder having retaining means connected to said plate, said retaining means generally maintaining said patch emplaced on said plate at said engaging means until removed and replaced, wherein said engaging means conform to said retaining means.

3. The system according to claim 2 wherein said retaining means further comprises a clasp attached as a spring means to said plate, said clasp releasably holding said patch engaging means, such that it is emplaced on said plate.

4. A system for replaceably retaining an intra-oral medication device such as an intra-oral fluoride device in the mouth comprising:

a holder having a retaining member with a back surface, said back surface attachable to a post extending from said back surface, said post attachable to a tooth; and clasp means on said retaining member for maintaining said device on said back surface.

* * * * *